(12) United States Patent
Nebrigic et al.

(10) Patent No.: US 8,788,060 B2
(45) Date of Patent: Jul. 22, 2014

(54) TISSUE TREATMENT SYSTEMS WITH HIGH POWERED FUNCTIONAL ELECTRICAL STIMULATION AND METHODS FOR REDUCING PAIN DURING TISSUE TREATMENTS

(75) Inventors: Dragan Nebrigic, Carlsbad, CA (US); Thomas Markiewicz, Los Gatos, CA (US)

(73) Assignee: Solta Medical, Inc., Hayward, CA (US)

( * ) Notice: Subject to any disclaimer, the term of this patent is extended or adjusted under 35 U.S.C. 154(b) by 696 days.

(21) Appl. No.: 12/823,544

(22) Filed: Jun. 25, 2010

(65) Prior Publication Data

US 2011/0015687 A1 Jan. 20, 2011

Related U.S. Application Data

(60) Provisional application No. 61/226,145, filed on Jul. 16, 2009.

(51) Int. Cl.
*A61N 5/02* (2006.01)
*A61B 18/18* (2006.01)
*A61N 1/40* (2006.01)

(52) U.S. Cl.
CPC . *A61B 18/18* (2013.01); *A61N 1/40* (2013.01); *A61N 5/022* (2013.01); *A61N 5/02* (2013.01); *A61N 1/403* (2013.01)
USPC ............... 607/101; 607/100; 607/102; 606/9

(58) Field of Classification Search
CPC ........... A61B 18/18; A61N 5/02; A61N 1/40; A61N 5/025; A61F 7/007; A61F 2007/0052; A61F 2007/0071; A61F 2007/0087; A61F 2007/0242; A61F 2007/0282
USPC ............................................................ 606/9
See application file for complete search history.

(56) References Cited

U.S. PATENT DOCUMENTS

| 3,861,383 A | 1/1975 | Kovach |
| 4,014,347 A | 3/1977 | Halleck et al. |

(Continued)

FOREIGN PATENT DOCUMENTS

| AU | 779100 B2 | 9/2000 |
| CA | 2364098 A1 | 9/2000 |

(Continued)

OTHER PUBLICATIONS

Junger, M. et al., "Local therapy and treatment costs of chronic, venous leg ulcers with electrical stimulation (Dermapulse): a prospective, placebo controlled, double blind trial", Wound Rep Reg (2008) 480-487.

(Continued)

*Primary Examiner* — Linda Dvorak
*Assistant Examiner* — Kaitlyn Smith
(74) *Attorney, Agent, or Firm* — Wood, Herron & Evans, LLP

(57) ABSTRACT

Methods, apparatus, and systems for transcutaneously treating tissue located beneath a skin surface with electromagnetic energy delivered from a treatment electrode. A portion of the treatment electrode is contacted with the skin surface. While maintaining the contact between the portion of the treatment electrode and the skin surface, the electromagnetic energy is delivered from the treatment electrode in a plurality of power pulses through the skin surface to the tissue over a treatment time with a time gap between each consecutive pair of the pulses to lower a level of pain perceived by a patient.

11 Claims, 5 Drawing Sheets

(56) References Cited

U.S. PATENT DOCUMENTS

| | | | |
|---|---|---|---|
| 4,211,230 A * | 7/1980 | Woltosz | 606/40 |
| 4,595,008 A | 6/1986 | Guibert | |
| 5,447,530 A | 9/1995 | Guibert et al. | |
| 5,449,378 A | 9/1995 | Schouenborg | |
| 5,580,350 A | 12/1996 | Guibert et al. | |
| 5,660,836 A | 8/1997 | Knowlton | |
| 5,727,556 A | 3/1998 | Weth et al. | |
| 5,755,753 A | 5/1998 | Knowlton | |
| 5,871,524 A | 2/1999 | Knowlton | |
| 5,885,273 A * | 3/1999 | Eckhouse et al. | 606/9 |
| 5,919,219 A | 7/1999 | Knowlton | |
| 5,941,902 A | 8/1999 | Holcomb | |
| 5,948,009 A | 9/1999 | Tu | |
| 5,948,011 A | 9/1999 | Knowlton | |
| 5,997,530 A * | 12/1999 | Nelson et al. | 606/9 |
| 6,011,994 A | 1/2000 | Kronberg | |
| 6,063,079 A | 5/2000 | Hovda et al. | |
| 6,068,596 A | 5/2000 | Weth et al. | |
| 6,086,585 A | 7/2000 | Hovda et al. | |
| 6,091,989 A | 7/2000 | Swerdlow et al. | |
| 6,091,994 A | 7/2000 | Loos | |
| 6,104,959 A * | 8/2000 | Spertell | 607/101 |
| 6,109,268 A | 8/2000 | Thapliyal et al. | |
| 6,139,545 A | 10/2000 | Utley et al. | |
| 6,148,232 A | 11/2000 | Avrahami | |
| 6,210,402 B1 | 4/2001 | Olsen et al. | |
| 6,217,534 B1 | 4/2001 | Natalicio | |
| 6,228,078 B1 | 5/2001 | Eggers et al. | |
| 6,254,600 B1 | 7/2001 | Willink et al. | |
| 6,264,652 B1 | 7/2001 | Eggers et al. | |
| 6,277,116 B1 | 8/2001 | Utely et al. | |
| 6,296,638 B1 | 10/2001 | Davison et al. | |
| 6,309,387 B1 | 10/2001 | Eggers et al. | |
| 6,311,090 B1 | 10/2001 | Knowlton | |
| 6,334,074 B1 * | 12/2001 | Spertell | 607/101 |
| 6,350,276 B1 * | 2/2002 | Knowlton | 607/104 |
| 6,387,380 B1 | 5/2002 | Knowlton | |
| 6,405,090 B1 | 6/2002 | Knowlton | |
| 6,408,212 B1 | 6/2002 | Neev | |
| 6,413,255 B1 * | 7/2002 | Stern | 606/41 |
| 6,432,103 B1 | 8/2002 | Ellsberry et al. | |
| 6,445,955 B1 | 9/2002 | Michelson et al. | |
| 6,453,202 B1 | 9/2002 | Knowlton | |
| 6,461,350 B1 | 10/2002 | Underwood et al. | |
| 6,461,354 B1 | 10/2002 | Olsen et al. | |
| 6,535,767 B1 | 3/2003 | Kronberg | |
| 6,544,261 B2 | 4/2003 | Ellsberry et al. | |
| 6,572,594 B2 | 6/2003 | Satterfield et al. | |
| 6,659,106 B1 | 12/2003 | Hovda et al. | |
| 6,679,908 B2 | 1/2004 | Shimizu | |
| 6,697,670 B2 | 2/2004 | Chomenky et al. | |
| 6,719,754 B2 | 4/2004 | Underwood et al. | |
| 6,746,447 B2 | 6/2004 | Davison et al. | |
| 6,749,624 B2 * | 6/2004 | Knowlton | 607/104 |
| 6,766,202 B2 | 7/2004 | Underwood et al. | |
| 6,832,996 B2 | 12/2004 | Woloszko et al. | |
| 6,843,789 B2 | 1/2005 | Goble | |
| 6,866,678 B2 * | 3/2005 | Shenderova et al. | 607/88 |
| 6,896,672 B1 | 5/2005 | Eggers et al. | |
| 6,902,554 B2 | 6/2005 | Huttner | |
| 6,916,316 B2 * | 7/2005 | Jay | 606/9 |
| 6,920,883 B2 | 7/2005 | Bessette et al. | |
| 6,930,590 B2 | 8/2005 | Ling et al. | |
| 6,949,096 B2 | 9/2005 | Davison et al. | |
| 6,991,631 B2 | 1/2006 | Woloszko et al. | |
| 7,001,381 B2 | 2/2006 | Harano et al. | |
| 7,004,941 B2 | 2/2006 | Tvinnereim et al. | |
| 7,020,528 B2 | 3/2006 | Neev | |
| 7,117,034 B2 | 10/2006 | Kronberg | |
| 7,131,969 B1 | 11/2006 | Hovda et al. | |
| 7,147,654 B2 * | 12/2006 | Baumgardner et al. | 607/88 |
| 7,217,267 B2 * | 5/2007 | Jay | 606/18 |
| 7,241,293 B2 | 7/2007 | Davison | |
| 7,300,436 B2 * | 11/2007 | Penny et al. | 606/34 |
| 7,331,957 B2 | 2/2008 | Woloszko et al. | |
| 7,389,145 B2 | 6/2008 | Kilgore et al. | |
| 7,422,586 B2 | 9/2008 | Morris et al. | |
| 7,452,358 B2 | 11/2008 | Stern et al. | |
| 7,473,251 B2 | 1/2009 | Knowlton et al. | |
| 7,510,555 B2 * | 3/2009 | Kanzius | 606/33 |
| 7,601,149 B2 | 10/2009 | DiCarlo et al. | |
| 7,699,058 B1 * | 4/2010 | Jay | 128/898 |
| 7,722,600 B2 * | 5/2010 | Connors et al. | 606/9 |
| 7,762,964 B2 | 7/2010 | Slatkine | |
| 7,762,965 B2 | 7/2010 | Slatkine | |
| 7,824,394 B2 | 11/2010 | Manstein | |
| 8,073,550 B1 * | 12/2011 | Spertell | 607/101 |
| 8,216,218 B2 | 7/2012 | Burns et al. | |
| 8,287,579 B2 * | 10/2012 | Nimitz | 607/104 |
| 8,367,959 B2 * | 2/2013 | Spertell | 219/52 |
| 8,406,894 B2 * | 3/2013 | Johnson et al. | 607/101 |
| 8,540,705 B2 * | 9/2013 | Mehta | 606/32 |
| 8,579,896 B2 * | 11/2013 | Kreindel | 606/49 |
| 8,647,338 B2 * | 2/2014 | Chornenky et al. | 606/32 |
| 2001/0025176 A1 | 9/2001 | Ellsberry et al. | |
| 2002/0087155 A1 | 7/2002 | Underwood et al. | |
| 2002/0133149 A1 | 9/2002 | Bessette | |
| 2002/0169442 A1 * | 11/2002 | Neev | 606/9 |
| 2002/0193789 A1 | 12/2002 | Underwood et al. | |
| 2003/0117371 A1 | 6/2003 | Roberts et al. | |
| 2003/0208194 A1 | 11/2003 | Hovda et al. | |
| 2003/0212351 A1 | 11/2003 | Hissong et al. | |
| 2003/0212396 A1 | 11/2003 | Eggers et al. | |
| 2003/0225403 A1 | 12/2003 | Woloszko et al. | |
| 2003/0236487 A1 | 12/2003 | Knowlton | |
| 2004/0098065 A1 | 5/2004 | Hagglof et al. | |
| 2004/0127895 A1 | 7/2004 | Flock et al. | |
| 2004/0206365 A1 | 10/2004 | Knowlton | |
| 2004/0210214 A1 | 10/2004 | Knowlton | |
| 2005/0055055 A1 * | 3/2005 | Neev | 607/3 |
| 2005/0152905 A1 | 7/2005 | Omoigui | |
| 2005/0171581 A1 * | 8/2005 | Connors et al. | 607/88 |
| 2005/0217682 A1 | 10/2005 | Orton | |
| 2005/0234439 A1 | 10/2005 | Underwood | |
| 2005/0267454 A1 | 12/2005 | Hissong et al. | |
| 2005/0288665 A1 | 12/2005 | Woloszko | |
| 2006/0004306 A1 | 1/2006 | Altshuler et al. | |
| 2006/0025837 A1 * | 2/2006 | Stern et al. | 607/99 |
| 2006/0036300 A1 * | 2/2006 | Kreindel | 607/99 |
| 2006/0047281 A1 | 3/2006 | Kreindel | |
| 2006/0089688 A1 | 4/2006 | Panescu | |
| 2006/0142741 A1 * | 6/2006 | Jay | 606/3 |
| 2006/0171890 A1 | 8/2006 | Yeomans et al. | |
| 2006/0212077 A1 | 9/2006 | Pilla et al. | |
| 2006/0217636 A1 | 9/2006 | Braig et al. | |
| 2006/0293722 A1 | 12/2006 | Slatkine et al. | |
| 2007/0010811 A1 | 1/2007 | Stern et al. | |
| 2007/0049998 A1 * | 3/2007 | Conrad et al. | 607/96 |
| 2007/0060921 A1 | 3/2007 | Janssen et al. | |
| 2007/0066971 A1 | 3/2007 | Podhajsky | |
| 2007/0078290 A1 | 4/2007 | Esenaliev | |
| 2007/0093797 A1 | 4/2007 | Chan et al. | |
| 2007/0093798 A1 | 4/2007 | DeBenedictis et al. | |
| 2007/0142863 A1 | 6/2007 | Bradley | |
| 2007/0167943 A1 | 7/2007 | Janssen et al. | |
| 2007/0219604 A1 | 9/2007 | Yaroslavsky et al. | |
| 2007/0219605 A1 | 9/2007 | Yaroslavsky et al. | |
| 2007/0282318 A1 * | 12/2007 | Spooner et al. | 606/32 |
| 2008/0015565 A1 | 1/2008 | Davison | |
| 2008/0015568 A1 | 1/2008 | Paul et al. | |
| 2008/0058784 A1 | 3/2008 | Manstein et al. | |
| 2008/0091179 A1 | 4/2008 | Durkin et al. | |
| 2008/0119828 A1 | 5/2008 | Nelson et al. | |
| 2008/0183251 A1 * | 7/2008 | Azar et al. | 607/101 |
| 2008/0188779 A1 | 8/2008 | Vallero | |
| 2008/0200969 A1 * | 8/2008 | Weber | 607/102 |
| 2008/0214968 A1 | 9/2008 | Milne et al. | |
| 2008/0215039 A1 | 9/2008 | Slatkine et al. | |
| 2008/0269851 A1 * | 10/2008 | Deem et al. | 607/101 |
| 2008/0288035 A1 | 11/2008 | Gill et al. | |
| 2008/0294226 A1 | 11/2008 | Moffitt et al. | |
| 2008/0306418 A1 | 12/2008 | DeBenedictis et al. | |
| 2009/0076572 A1 * | 3/2009 | Nimitz | 607/96 |
| 2009/0149930 A1 * | 6/2009 | Schenck | 607/100 |

(56) References Cited

U.S. PATENT DOCUMENTS

| | | | |
|---|---|---|---|
| 2009/0171424 A1 | 7/2009 | Britva et al. | |
| 2009/0270954 A1* | 10/2009 | Schenck | 607/102 |
| 2009/0287207 A1 | 11/2009 | Stern et al. | |
| 2009/0318909 A1* | 12/2009 | DeBenedictis et al. | 606/9 |
| 2010/0145321 A1 | 6/2010 | Altshuler et al. | |
| 2010/0179455 A1 | 7/2010 | Nebrigic et al. | |
| 2010/0179531 A1 | 7/2010 | Nebrigic et al. | |
| 2010/0204619 A1* | 8/2010 | Rosenberg | 601/3 |
| 2010/0228243 A1* | 9/2010 | Mehta | 606/33 |
| 2011/0015687 A1* | 1/2011 | Nebrigic et al. | 607/3 |
| 2011/0137307 A1* | 6/2011 | Imran | 606/41 |
| 2011/0172586 A1 | 7/2011 | Hennings et al. | |
| 2011/0196363 A1* | 8/2011 | Kreindel | 606/33 |
| 2011/0202048 A1 | 8/2011 | Nebrigic | |
| 2012/0022622 A1* | 1/2012 | Johnson et al. | 607/101 |
| 2012/0041432 A1* | 2/2012 | Spertell | 606/33 |
| 2012/0303020 A1* | 11/2012 | Chornenky et al. | 606/41 |
| 2013/0066406 A1* | 3/2013 | Spertell | 607/102 |
| 2013/0150841 A1* | 6/2013 | Schomacker et al. | 606/13 |
| 2013/0166003 A1* | 6/2013 | Johnson et al. | 607/101 |

FOREIGN PATENT DOCUMENTS

| | | |
|---|---|---|
| EP | 1158919 | 12/2001 |
| EP | 1407720 A1 | 4/2004 |
| JP | 11504828 | 5/1999 |
| JP | 2002537939 A | 11/2002 |
| JP | 2007268297 A | 10/2007 |
| WO | 9634568 A1 | 11/1996 |
| WO | 0053113 | 9/2000 |
| WO | 2008069647 A1 | 6/2008 |

OTHER PUBLICATIONS

Kim YH et al., "Effect of pulsed radiofrequency for postherpetic neuralgia", Acta Anaesthesiol Scand 2008; 52: 1140-1143, Singapore.

Van Zundert, J. et al., "Pulsed radiofrequency adjacent to the cervical dorsal root ganglion in chronic cervical radicular pain: a double blind sham controlled randomized clinical trial", Pain 127 (2007) 173-182.

Rosted P. et al., "Use of Stimulation techniques in pain treatment", Ugeskr Laeger. May 15, 2006; 168(20):1982-6 (abstract only of Danish article).

Apkarian, AV et al., "Heat-induced pain diminishes vibrotactile perception: a touch gate", Somatosensory and Motor Research, vol. 11, No. 3, 1994, pp. 259-267.

Pevzner et al., "Pulsed radiofrequency treatment of severe radicular pain", Harefuah. Mar. 2005;144(3):178-80, 231. (article in Hebrew).

Mikeladze et al, "Pulsed radiofrequency application in treatment of chronic zygapophyseal joint paint", The Spine Journal 3 (2003) 360-362.

Fisher GH et al., "Concurrent use of a handheld forced cold air device minimizes pteient discomfort during fractional photothermolysis", Dermatol Surg 2005, 31:1242-1244.

Maeda Y. et al, "Low frequencies, but not high frequencies of bi-polar spinal cord stimulation reduce cutaneous and muscle hyperalgesia induced by nerve injury", Pain 138 (2008) 143-152.

Rottmann S. et al, "Electrical low-frequency stimulation induces homotopic long-term depression of nociception and pain from hand in man", Clinical Neurophysiology 119 (2008) 1895-1904.

Gold, MH, "Treatment of wrinkles and elastosis using vacuum-assisted bipolar radiofrequency heating of the dermis", Dermatol Surg 2007; 33:300-309.

Gildenberg, PL "History of electrical neuromodulation for chronic pain", Pain Medicine, vol. 7, No. S1, 2006.

Ersek, RA, "Transcutaneous electrical neurostimulation: a new therapeutic modality for controlling pain", Clinical Orthopaedics and Related Research, Oct. 1977, vol. 128, 314-324, Section II: General Orthopaedics.

Fletcher, H. "Painless Depo-medroxyprogresterone acetate (DMPA) injections using the 'pinch technique'" Journal of Obstetrics and Gynaecology (Aug. 2004) vol. 24, No. 5, 562-563.

Saijo, M. et al., "Lack of pain reduction by a vibrating local anesthetic attachment: a pilot study" Anesth Prog 52:62-64 2005.

USPTO, Office Action issued in related U.S. Appl. No. 12/134,009 dated Mar. 1, 2012.

Ersek, "Transcutaneous Electrical Neurostimulation: A New Therapeutic Modality for Controlling Pain," Clin. Ortop. Relat. Res., 1977, 128:314-24.

Fletcher, "Painless Depo-Medroxyprogesterone Acetate (DMPA) Injections Using the 'Pinch Technique,'" J. Obstet. Gynaecol., 2004, 24(5):562-3.

International Search Report and Written Opinion, PCT/US08/65983, Oct. 1, 2008, 9 pages.

Saijo et al., "Lack of Pain Reduction by a Vibrating Local Anesthetic Attachment: A Pilot Study," Aneth. Prog., 2005, 52(2):62-4.

U.S. Appl. No. 60/942,175, filed Jun. 5, 2007, Leonard C. DeBenedictis.

USPTO, Office Action issued in related U.S. Appl. No. 12/823,214 dated Jul. 23, 2012.

Office Action issued in related U.S. Appl. No. 12/649,781 dated Jul. 24, 2012.

USPTO, Office Action issued in related U.S. Appl. No. 12/823,214 dated Jun. 6, 2013.

USPTO, Notice of Allowance issued in U.S. Appl. No. 12/649,781 dated Apr. 23, 2013.

Theodore J. Stigell, Office Action issued in related U.S. Appl. No. 12/649,781 dated Jan. 4, 2013.

USPTO, Office Action issued in related U.S. Appl. No. 12/823,214 dated Jan. 31, 2013.

USPTO, Office Action issued in U.S. Appl. No. 12/649,909 dated Sep. 17, 2013.

USPTO, Office Action issued in U.S. Appl. No. 13/941,077 dated Dec. 11, 2013.

USPTO, final Office Action issued in U.S. Appl. No. 12/823,214 dated Jan. 6, 2014.

* cited by examiner

TISSUE TREATMENT SYSTEMS WITH HIGH POWERED FUNCTIONAL ELECTRICAL STIMULATION AND METHODS FOR REDUCING PAIN DURING TISSUE TREATMENTS

CROSS-REFERENCE TO RELATED APPLICATIONS

This application claims the benefit of U.S. Provisional Application No. 61/226,145, filed Jul. 16, 2009, the disclosure of which is hereby incorporated by reference herein in its entirety.

BACKGROUND

The invention generally relates to systems and methods for treating tissue with high frequency energy and, more particularly, relates to systems and methods for reducing patient pain while treating tissue with high frequency energy.

Various cosmetic tissue treatments use energy delivery devices to non-invasively and non-ablatively treat tissue in order to improve a patient's appearance, such as smoothing and tightening skin; contouring along the jaw line and under the chin, and improving skin texture; softening wrinkles around the mouth, eyes and forehead; reducing cellulite; or removing skin spots or hair. These non-invasive, transcutaneous procedures involve no surgery or injections but instead project electromagnetic energy into the tissue. Such non-invasive energy delivery devices may emit the electromagnetic energy in different regions of the electromagnetic spectrum to accomplish the tissue treatment with reduced patient recovery time in comparison with ablative procedures.

Skin is a type of body tissue that includes plural distinct layers. The epidermis constitutes the visible outer layer on the surface. The dermis, which underlies the epidermis, contains collagen fibers, blood vessels, hair follicles, and other skin components. The hypodermis or subcutaneous fat layer, which underlies the demis, consists of fat tissue and a web of collagen fibers in the form of fibrous septae running through the fat. The fibrous septae secure the dermis to the underlying bone and muscle. Collagen fibers are recognized to be a very flexible and stretchable protein and are characterized by a high tensile strength.

The occurrence of wrinkles is an unavoidable natural process. Wrinkles are primarily associated with advancing age and skin damage arising from exposure to damaging environmental factors. Environmental factors include sun damage from exposure to sunlight, air pollution, smoking, repetitive facial movements such as frowning, and the natural effects of gravity, which cause sagging of the skin with advancing aging. Deteriorating collagen exhibits a loss of elasticity, which results in the formation of rhytids or wrinkling of the epidermis.

Electromagnetic radiation, specifically light and heat, applied to the different layers of the skin can have a physiological effect on the skin's appearance. In particular, electromagnetic energy can arrest the formation of wrinkles and impart a more youthful skin appearance. High frequency treatment devices, such as radio-frequency (RF)-based treatment devices, may be used to treat skin tissue non-ablatively and non-invasively with heat. Such high frequency devices operate by transmitting high frequency energy through the epidermis to the underlying tissue, while actively cooling the epidermis to prevent thermal damage to a depth of the skin tissue near the skin surface. The high frequency energy heats the tissue at depths beneath the cooled region to a therapeutic temperature sufficient to denature the collagen, which causes the collagen fibers in the dermis to shrink and contract. In addition to the tightening of the treated tissue as the collagen fibers contract, treatment with high frequency energy also causes a mild inflammation. The inflammatory response of the treated tissue may cause new collagen to be generated over time, which can result in additional tissue contraction. When the inflammatory response of the treated tissue is highly significant, the new collagen formed is known as scar collagen.

Conventional high frequency treatment devices employ a handpiece, a disposable treatment tip coupled with a nose of the handpiece, and a high frequency generator connected by conductors inside the handpiece with an electrode in the treatment tip. Conventional electrodes consist of a pattern of one or more metallic features carried on a flexible electrically insulating substrate, such as a thin film of polyimide. The substrate contacts the patient's skin surface during treatment and the metallic features reside on the non-contact side of the substrate. The temperature of the treatment tip, which is measured by temperature sensors carried on the treatment tip, is correlated with the temperature of the patient's skin During the procedure, the doctor controls the energy density of the high frequency power delivered from the electrode with a treatment setting. Treatment tips are frequently intended for single patient use and, therefore, are not reusable. Following the patient treatment, the doctor or treatment technician removes the treatment tip from the handpiece and, if disposable, discards it.

Patient pain is inherent in tissue treatments using electromagnetic energy. Patient pain is typically regulated to optimize the treatment result while also minimizing patient discomfort to make the procedure tolerable. A patient may be given an oral pain medication and/or a local topical anesthesia cream may be applied as a numbing agent. At the inception of the treatment procedure, the doctor will initially administer the high frequency energy at a treatment setting to one or more test sites and monitor patient feedback on the heat sensation associated with the treatment setting being used. A tolerable, yet comfortable, treatment setting for the treatment procedure is established based upon the patient feedback from the test sites.

The treatment electrode used in the treatment includes a conductor region delimited by an outer peripheral edge. For monopolar energy delivery, an edge effect has been observed at the outer peripheral edge that causes the energy density of the high frequency energy delivered to the tissue to be non-uniform across the surface area of the treatment electrode. Specifically, the energy density is highest near the peripheral edge of the electrode. As a result, tissue proximate to the outer peripheral edge of the electrode is heated to a higher temperature than tissue proximate to the interior surface area of the electrode. The higher temperatures near the peripheral edge form hot spot thermal zones that are a highly likely source of heat-related pain perceived by the patient. Because patient discomfort is linked with the treatment setting, reducing the treatment level to counteract the edge effect effectively reduces the average energy density for the high frequency energy delivered during the treatment procedure.

In general, treatment results and the chance for pain or discomfort will scale with the treatment setting used by the doctor. What is needed, therefore, are apparatus and methods for reducing the pain associated with such tissue treatments so that patient discomfort is alleviated and therapeutic results can be improved by increasing the treatment setting and the amount of heat delivered to the skin

SUMMARY OF THE INVENTION

The invention is generally directed to apparatus and methods that deliver electromagnetic energy to transcutaneously treat tissue underlying a skin surface with electromagnetic energy, particularly during non-invasive and non-ablative therapeutic tissue treatments with reduced patient pain.

In one embodiment, a method is provided for operating a tissue treatment apparatus to transcutaneously treat tissue located beneath a skin surface with electromagnetic energy delivered from a treatment electrode. The method includes contacting a portion of the treatment electrode with the skin surface. While maintaining the contact between the portion of the treatment electrode and the skin surface, the method further includes delivering the electromagnetic energy from the treatment electrode in a plurality of power pulses through the skin surface to the tissue over a treatment time with at least one time gap between consecutive pairs of the pulses.

In one embodiment, the delivery of the electromagnetic energy from the treatment electrode is discontinued during each time gap. In another embodiment, a power of the electromagnetic energy delivered in each of the power pulses has a constant magnitude.

In an embodiment, the method may further include measuring an attribute of the tissue, such as tissue temperature or tissue impedance and the adjusting a power of the electromagnetic energy delivered in each of the power pulses based upon the measured attribute. In another embodiment, the method may include delivering a cryogen pulse to the portion of the treatment electrode in the time gap between at least one of the consecutive pairs of power pulses. The cryogen pulse may cool the portion of the treatment electrode and the cooling of the portion of the treatment electrode may be communicated to the skin surface contacted by the portion of the treatment electrode so that a portion of the tissue underlying the skin surface is cooled.

In an embodiment, the method may further include delivering a cryogen pulse to the portion of the treatment electrode in the time gap between each of the consecutive pairs of power pulses. The cryogen pulse may cool the portion of the treatment electrode and the cooling of the portion of the treatment electrode may be communicated to the skin surface contacted by the portion of the treatment electrode so that a portion of the tissue underlying the skin surface is cooled.

The method may further include cooling the tissue in the time gap between at least one of the consecutive pairs of power pulses or cooling the tissue in the time gap between each consecutive pair of pulses.

The electromagnetic energy delivered to the tissue may have an operating frequency ranging from 200 kHz to 20 MHz, and the power pulses may occur with a frequency in a range of 1 Hz to 10 Hz. Alternatively, the power pulses may occur at a frequency that is more than four orders of magnitude less than an operating frequency for the electromagnetic energy.

While the electromagnetic energy is delivered through the skin surface to the tissue from the treatment electrode in the plurality of power pulses over the treatment time, the portion of the treatment electrode and the skin surface may be sustained in a stationary contacting relationship.

In another embodiment, a system is provided for transcutaneously treating tissue located beneath a skin surface with electromagnetic energy. The system includes a generator of the electromagnetic energy and a treatment tip mechanically coupled in a removable manner with a handpiece. The treatment tip includes a treatment electrode having a portion configured to be placed in a contacting relationship with the skin surface. The treatment electrode is electrically connected with the generator to receive the electromagnetic energy from the generator and deliver the electromagnetic energy through the skin surface to the tissue. The system further includes a system controller in electrical communication with the generator. The system controller is configured to cause the generator to supply the electromagnetic energy to the treatment electrode for delivery through the skin surface to the tissue at a series of temporally discontinuous power pulses over a treatment time while the portion of the treatment electrode is in contact with the skin surface.

In one embodiment, the system controller is configured to discontinue the delivery of electromagnetic energy from the treatment electrode during the periods between the temporally discontinuous pulses. In another embodiment, the generator is configured to generate the electromagnetic energy at an operating frequency of 200 kHz to 20 MHz, and the system controller is configured to provide the a series of temporally discontinuous power pulses at a frequency in a range of 1 Hz to 10 Hz.

In an embodiment, the treatment tip includes a nozzle configured to deliver cryogen to the portion of the treatment electrode in the contacting relationship with the skin surface. The system may further comprise a cryogen supply connected with the nozzle in the treatment tip for supplying the cryogen under pressure to the nozzle and a valve, which may be located inside the handpiece, in electrical communication with the system controller. The valve is configured to control flow of the cryogen from the cryogen supply to the nozzle and is operated by the system controller to deliver metered amounts of cryogen from the nozzle to the portion of the treatment electrode. The system controller may be configured to cause the valve to cycle to deliver one of the metered amounts in a time gap between each of consecutive pairs of the temporally discontinuous power pulses.

DETAILED DESCRIPTION

Figure 1:
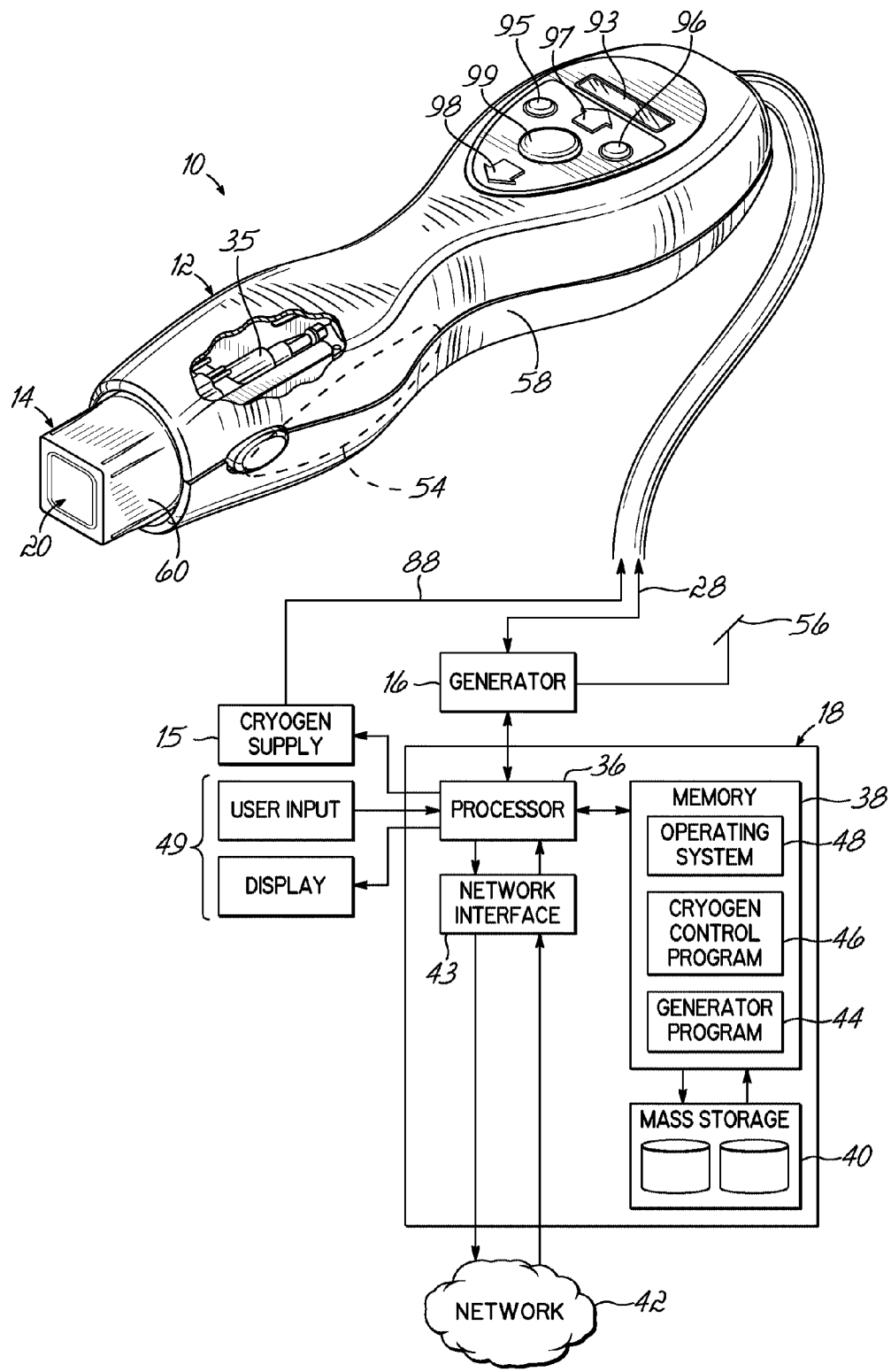
FIG. 1 is a diagrammatic view of a treatment system with a handpiece, a treatment tip, a control system, and a generator in accordance with an embodiment of the invention.

With reference to FIGS. 1, 2, 2A, 3 and 3A, a treatment apparatus 10 includes a handpiece 12, a treatment tip 14, a cryogen supply 15, a generator 16, and a system controller 18. The treatment tip 14 is coupled in a removable and releasable manner with the handpiece 12. The treatment tip 14 carries an electromagnetic energy delivery member in the representative form of a treatment electrode 20. In a representative embodiment, the treatment electrode 20 may include an electrically-insulating substrate 22 composed of a non-conductive dielectric material and a region 24 of an electrical conductor carried on the electrically-insulating substrate 22. In one embodiment, the substrate 22 of the treatment electrode 20 may comprise a thin flexible base polymer film carrying the conductor region 24 and conductive (e.g., copper) traces or leads 25 on the substrate 22 that are used to electrically couple the conductor region 24 with the generator 16 and temperature sensors 52 with the system controller 18. The base polymer film of substrate 22 may be, for example, polyimide or another material with a relatively high electrical resistivity and a relatively high thermal conductivity. Instead of the representative conductor region 24, the conductor region of treatment electrode 20 may be segmented into plural individual electrodes that can be individually powered to deliver electromagnetic energy to the tissue 30.

The conductor region 24 of the treatment electrode 20 is electrically coupled by a set of insulated and shielded conductors 28 that extend exteriorly of the handpiece 12 to the generator 16. The substrate 22 may also carry a non-volatile memory chip 27, such as an Erasable Programmable Read-Only Memory (EPROM), that retains its held data when unpowered. The memory chip 27 is coupled by the conductive leads 25 with the system controller 18.

The generator 16, which has the representative form of a high frequency power supply, is equipped with a conventional electrical circuit operative to generate high frequency electrical current, typically in the radio-frequency (RF) band of the electromagnetic spectrum. The operating frequency of generator 16 may be in the range of 200 kHz to about 20 MHz. In one embodiment, the generator 16 is a 400 watt, 6.78 MHz high frequency generator. The electrical circuit in the generator 16 converts a line alternating current voltage into drive signals for the treatment electrode 20. The drive signals have an energy content and a duty cycle appropriate for the amount of power and the mode of operation that have been selected by the clinician, as understood by a person having ordinary skill in the art.

The system controller 18 is interfaced with the cryogen supply 15 and with the generator 20, and coordinates the operation of the treatment apparatus 10. In particular, the system controller 18 regulates the power delivered from the generator 20 to the treatment electrode 16 by setting the operational parameters of the generator 20 and by setting the operational parameters of the cryogen supply 15. Under the control of the system controller 18 and operator interaction with controls at the system controller 18 and handpiece 12, the treatment apparatus 10 is adapted to non-invasively and non-ablatively deliver electromagnetic energy in a high frequency band of the electromagnetic spectrum, such as the radiofrequency (RF) band, to an underlying region of a patient's tissue 30.

Figure 3:
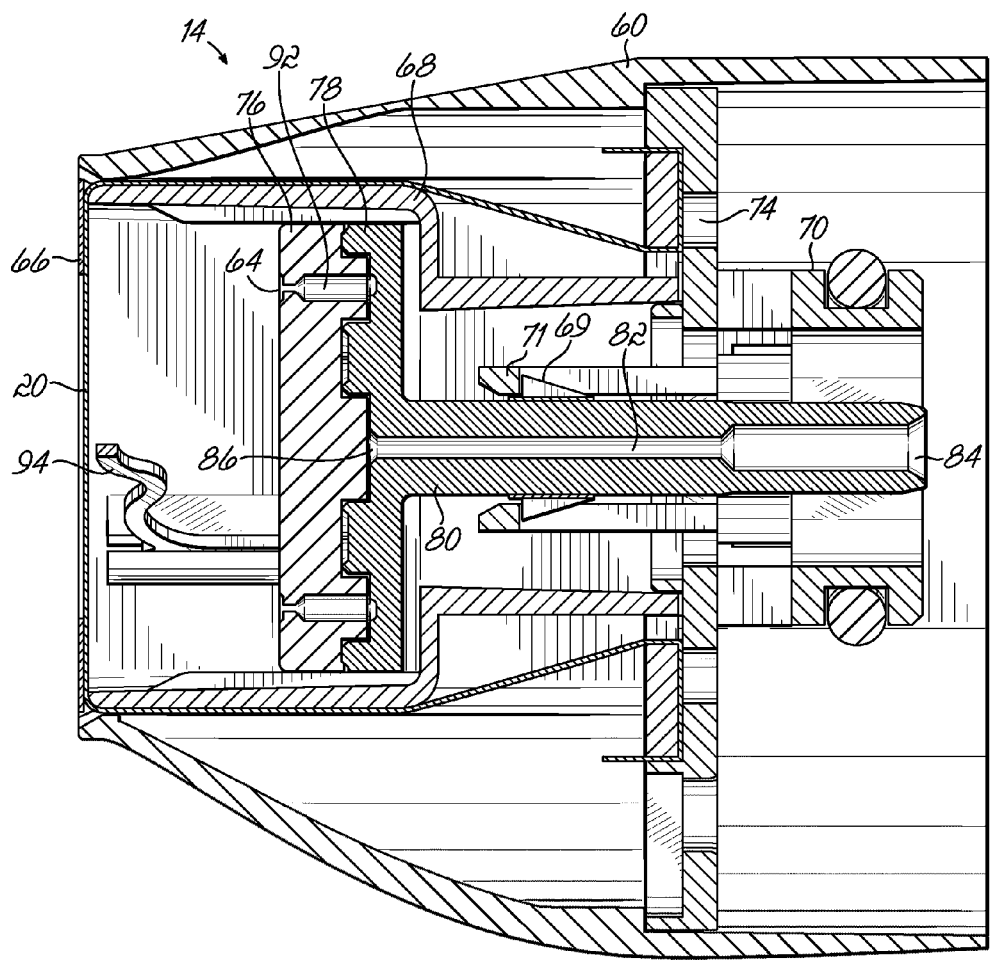
FIG. 3 is a diagrammatic cross-sectional view of the treatment tip of FIGS. 1 and 2.
Figure 3A:
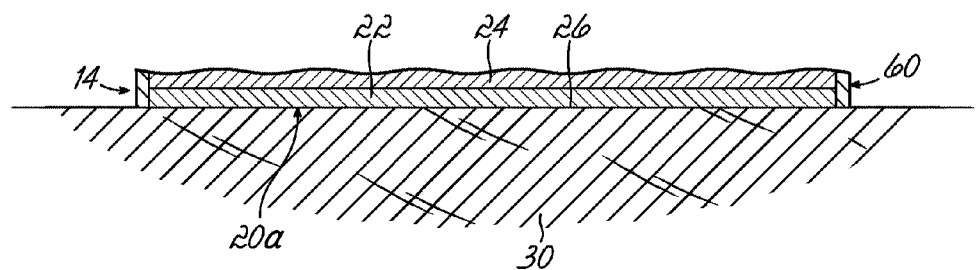
FIG. 3A is a cross-sectional view of a portion of the treatment tip in contact with the skin surface.

The electromagnetic energy imparts a therapeutic effect to heat tissue 30 in a targeted region 32 beneath the patient's skin surface 26, as best shown in FIG. 3A, to a therapeutic temperature. Because of the concurrent cooling from the skin surface 26 inward, a region 31 of the tissue 30 between region 32 and the skin surface 26 are heated to a non-therapeutic temperature such that this shallow tissue portion is not modified. The delivered energy volumetrically heats a region 32 of the tissue 30 to a targeted temperature range. The elevation in temperature within the heated region 32 may produce for example, changes in collagen in the tissue 30 that achieve a desired treatment result, such as removing or reducing wrinkles and otherwise tightening the skin to thereby improve the appearance of a patient receiving the treatment.

System controller 18 may represent practically any computer, computer system, or programmable device recognized by a person having ordinary skill in the art. System controller 18 typically includes at least one processor 36 coupled to a memory 38. Processor 36 may represent one or more processors (e.g., microprocessors), and memory 38 may represent the random access memory (RAM) devices comprising the main storage of system controller 18, as well as any supplemental levels of memory, e.g., cache memories, non-volatile or backup memories (e.g. programmable or flash memories), read-only memories, etc. In addition, memory 38 may be considered to include memory storage physically located elsewhere in system controller 18, e.g., any cache memory in processor 36, as well as any storage capacity used as a virtual memory, e.g., as stored on a mass storage device 40 or another computer (not shown) coupled to system controller 18 via a network interface 43 over a network 42. The system controller 18 operates under the control of an operating system 48, and executes or otherwise relies upon various computer software applications, components, programs, objects, modules, data structures, etc. (e.g., power modulation control program 44 or cryogen control program 46 executing in memory 38).

The system controller 18 includes digital and/or analog circuitry that interfaces with the cryogen supply 15 and the generator 20 for supplying control signals to the cryogen supply 15 and generator 20 and receiving feedback information from sensors that is used in generating the control signals. Cryogen control program 46 resident as an application in the memory 38 is executed as an algorithm by the processor 36 in order to issue commands that control the operation of the cryogen supply 15. Generator control program 44 resident as an application in the memory 38 is executed as an algorithm by the processor 36 in order to issue commands that control the operation of the generator 20. The mass storage device 40 may store a copy of the generator control program 44 and a copy of the cryogen control program 46.

The system controller 18 also typically receives a number of inputs and outputs for external communications of information. For interface with a user or operator, the system controller 18 typically includes one or more user interface devices 49, such as input devices (e.g., a keyboard, a mouse, a trackball, a joystick, a touchpad, a keypad, a stylus, and/or a microphone, among others). Interface devices 49 may also include a display or other output device (e.g., a CRT monitor, an LCD display panel, and/or a speaker, among others). The interface to the system controller 18 may also be through an external terminal connected directly or remotely to system controller 18, or through another single (or multi) user computer (not shown) communicating with the system controller 18 via network 42, modem, or other type of communications device. Instructions delivered to the system controller 18 via the user interface devices 49 may be used to adjust the generator 16 to establish an arbitrary treatment setting. Information displayed by the user interface devices 49 may include the amount of energy delivered, tissue impedance, duration, and feedback to the operator relating to procedure technique. System controller 18 may optionally be linked with a nonvolatile memory (not shown) carried by the handpiece 12 or with a nonvolatile memory (not shown) carried by the treatment tip 14.

In general, the routines executed to implement the embodiments of the invention, whether implemented as part of an operating system or a specific application, component, program, object, module or sequence of instructions will be referred to herein as "computer program code", or simply "program code". The computer program code typically comprises one or more instructions that are resident at various times in various memory and storage devices in a computer, and that, when read and executed by one or more processors in a computer, causes that computer to perform the steps necessary to execute steps or elements embodying the various aspects of the invention. Moreover, while the invention has and hereinafter will be described in the context of fully functioning computers and computer systems, those skilled in the art will appreciate that the various embodiments of the invention are capable of being distributed as a program product in a variety of forms, and that the invention applies equally regardless of the particular type of computer readable media used to actually carry out the distribution. Examples of computer readable media include but are not limited to physical, recordable type media such as volatile and non-volatile memory devices, floppy and other removable disks, hard disk drives, optical disks (e.g., CD-ROM's, DVD's, etc.), among others, and transmission type media such as digital and analog communication links. In one embodiment, the information on the computer readable media is non-transitory.

During a non-ablative and non-invasive tissue treatment, a portion of one side or surface 50 of the treatment electrode 20 is placed into a directly contacting relationship with the skin surface 26 of the patient. The conductor region 24 of the treatment electrode 20 is physically carried on a non-contact side or surface 51 of the substrate 22 of the treatment electrode 20 and is therefore separated by the substrate 22 from the skin surface 26 (FIG. 3A). Hence, in the representative embodiment, the substrate 22 is arranged between the conductor region 24 and the skin surface 26. Electromagnetic energy is transmitted in a transcutaneous manner from the conductor region 24 on one side 51 of the substrate 22 through the thickness of substrate 22 across the area of the surface 50 registered with the conductor region 24 to the corresponding surface area of skin surface 26 and the underlying tissue 30 by capacitively coupling with the tissue 30.

The treatment tip 14 includes a plurality of sensors 52 that output readings that are used as feedback by the system controller 18 to control the treatment process. In one embodiment, the sensors are temperature sensors 52, such as thermistors or thermocouples, that are constructed to detect the temperature of the treatment electrode 20 and/or treatment tip 14. In the representative embodiment, the temperature sensors 52 are disposed on the surface 51. The measured temperature reflects the temperature of the treated tissue 30 and may be used as feedback in a control loop by the system controller 18 for controlling energy delivery and/or cooling of the skin surface 26. The handpiece 12 or treatment tip 14 may also include pressure sensors (not shown) for detecting physical contact between the treatment electrode 20 and the skin surface 26. In an alternative embodiment, one or more of the sensors 52 may be impedance sensors.

An activation button 54, which is accessible to the operator from the exterior of the handpiece 12, is configured to be actuated to close a switch in a normally open circuit with the generator 16. The closed circuit energizes the treatment electrode 20. Actuation of the activation button 54 triggers delivery of a dose of the high frequency energy over a short timed delivery cycle to the target tissue 30. After a lapsed treatment time, the delivery of high frequency energy from the treatment electrode 20 to the tissue 30 at the treatment site is discontinued and the handpiece 12 is manipulated to position the treatment tip 14 near a different treatment site on the skin surface 26. Another cycle is then initiated to deliver another dose of high frequency energy to the patient's tissue 30. As described hereinbelow, the delivery of high frequency energy is modulated to be discontinuous over each individual treatment time. The treat and move process is repeated for an arbitrary number of treatment sites distributed across the skin surface 26.

High frequency electrical current flowing between the treatment electrode 20 and the patient is concentrated at the skin surface 26 and within the underlying tissue 30 across the contacting surface area of the treatment electrode 20. Capacitive coupling of the high frequency electromagnetic energy relies on energy transfer through the dielectric material of the substrate 22 to create an electric field across the surface area where the treatment electrode 20 contacts the patient's body. The time-varying electric field induces electrical currents within the surrounding tissue 30 beneath the skin surface 26. Because of the natural resistance of tissue 30 to electrical current flow, volumetric heating results within the tissue 30. The volumetric heating delivers a therapeutic effect to the region 32 of the tissue 30 near the treatment site. For example, heating to a temperature of 60° C. or higher may contract collagen fibers and/or form nascent collagen within the region 32, which will result in tissue tightening or another aesthetic effect to improve the patient's appearance. The heating depth in the tissue 30 is based upon the size and geometry of the treatment electrode 20 and, contingent upon the selection and configuration of the treatment tip 14 and cooling with a reverse thermal gradient, can be controlled to extend from a few hundred microns beneath the skin surface 26 to several millimeters.

A non-therapeutic passive return electrode 56 is used to electrically couple the patient with the generator 16. During patient treatment, the high frequency current flows from the treatment electrode 20 through the treated tissue 30 and the intervening bulk of the patient to the return electrode 56 and then to the generator 16 through the conductors 22 to define a closed circuit or current path. The return electrode 56 is physically attached by, for example, adhesive to a site on the body surface of the patient, such as the patient's back. The surface area of the return electrode 56 in contact with the patient is relatively large in comparison with the surface area of the treatment electrode 20. Consequently, at the tissue adjacent to the return electrode 56, the current density flowing from the patient to the return electrode 56 is distributed across the larger surface area and is relatively low in comparison with the current density flowing from the treatment electrode 20 of smaller surface area to the patient. Because negligible heating is produced at its attachment site to the patient, a non-therapeutic effect is created in the tissue adjacent to the return electrode 56.

Although the treatment electrode 20 and the return electrode 56 are representatively configured for the delivery of monopolar high frequency energy, the treatment electrode 20 may be configured to deliver bipolar high frequency energy. The modifications to the treatment apparatus 10 required to deliver bipolar high frequency energy are familiar to a person having ordinary skill in the art. For example, the return electrode 56 may be eliminated from the treatment apparatus 10 and a bipolar treatment electrode substituted for the monopolar treatment electrode 20.

With continued reference to FIGS. 1, 2, 2A, 3, and 3A, the handpiece 12 is constructed from an outer housing 58 and the treatment tip 14 includes an outer housing 60 that is mechanically coupled with the housing 58 to establish an assembly. The handpiece 12 and treatment tip 14 include complementary electrical/fluid interfaces (not shown) that are coupled together when the housings 58, 60 are mechanically coupled. The housings 58, 60 may be fabricated by an injection molding process using a suitable polymer resin as a construction material. The handpiece 12 has a smoothly contoured shape suitable for gripping and manipulation by an operator. The operator maneuvers the treatment tip 14 and treatment electrode 20 to a location proximate to the skin surface 26 and, typically, to place the treatment electrode 20 in a contacting relationship with the skin surface 26.

Figure 2:
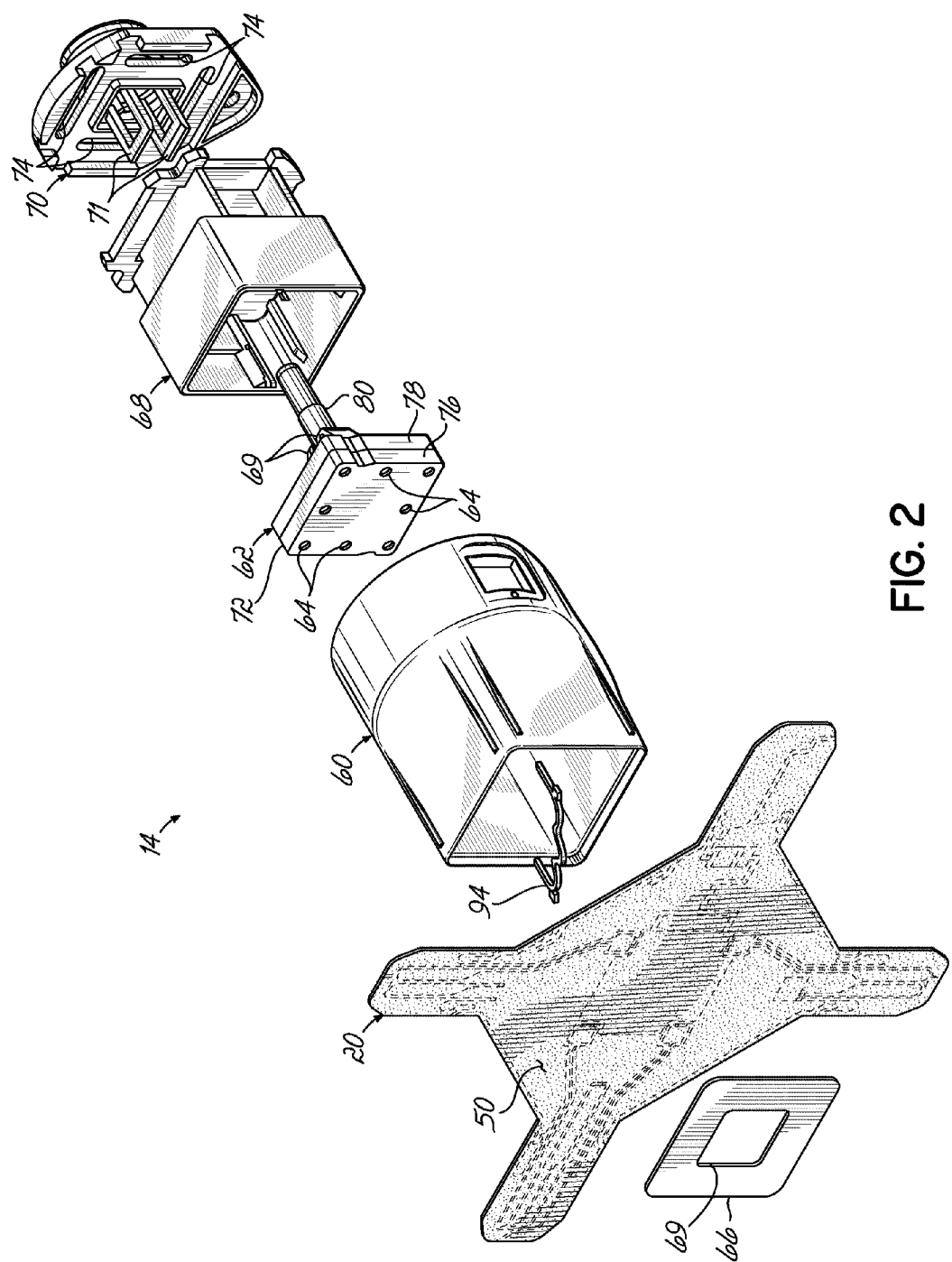
FIG. 2 is an exploded view of the treatment tip of FIG. 1.
Figure 2A:
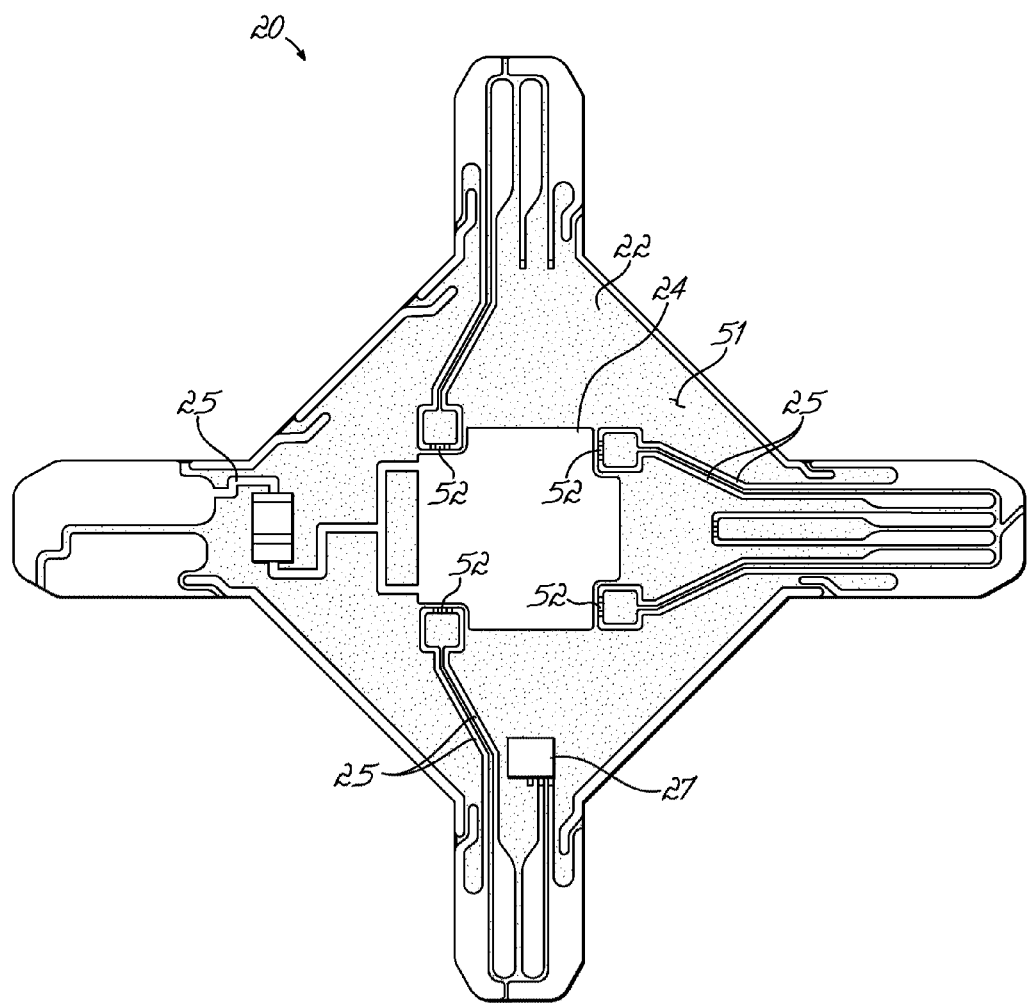
FIG. 2A is a view of the backside of the treatment electrode.

With reference to FIGS. 2 and 3, the treatment tip 14 includes the treatment electrode 20, the housing 60, a nozzle 62 that is configured with a head 72 having multiple orifices 64, a tip frame 66 that is coupled with the treatment electrode 20, and a pair of structural members 68, 70 that support the nozzle 62. The structural member 68, 70 are assembled with the nozzle 62 such that the head 72 of the nozzle 62 is recessed inside the similarly shaped hollow interior of the structural member 68. The assembly of the treatment electrode 20 and structural members 68, 70 is secured together by complementary clip fasteners 69, 71 on the nozzle 62 and structural member 70. The treatment electrode 20, which is shown in an unfolded state, is wrapped about the exterior of the structural member 68 such that the leads 25 can be contacted through openings 74 defined in structural member 70. A bridge 94 provides backside mechanical support and rigidity to the flexible treatment electrode 20. An optional heat spreader (not shown) may be disposed between the head 72 and the treatment electrode 20. The tip frame 66 has a central aperture 69 that is registered with the conductor region 24 of the treatment electrode 20.

The nozzle 62 is an assembly that includes a spray plate 76, a flange 78 that is coupled with the spray plate 76 to define the head 72, and a stem 80 that extends rearwardly from the flange 78. Extending axially along the length of the stem 80 is a flow channel 82 with an inlet 84 and an outlet 86. Cryogen is pumped from the cryogen supply 15 through tubing 88 partially inside the handpiece 12 and mechanically coupled with the inlet 84 to the flow channel 82. The cryogen supply 15 may be a pre-filled canister containing a pressurized cryogen like the low boiling point fluids 1,1-Difluoroethane (R-152a refrigerant) or 1,1,1,2-Tetrafluoroethane (R-134a refrigerant). Disposed between the flange 78 and spray plate 76 is a system of flow channels 90 that distributed the cryogen to passages 92 extending through the thickness of the spray plate 76. Each of the passages 92 terminates at one of the orifices 64.

The cryogen is ejected in a pulse as an atomized or non-atomized stream of coolant from each of the orifices 64 toward the backside 51 of the treatment electrode 20 and, in particular, toward the conductor region 24. The cryogen impinges and wets the backside 51 of the treatment electrode 20 and subsequently evaporates, which extracts heat and produces the cooling. Because of the low thermal mass, the temperature of the treatment electrode 20 drops rapidly upon evaporation. The cooling effect from the reduced temperature is communicated through the substrate 22 to the skin surface 26 and into the tissue 30 to extract heat from the tissue 30. The cooling competes with the volumetric heating from the high frequency energy such that a reverse thermal gradient is produced in tissue 30 and the therapeutic effect is delivered only to the region 32. The cooling of the reverse thermal gradient protects the region of tissue 30 between region 32 and the skin surface 26 from reaching a therapeutic temperature. The cooling is superimposed on the heating profile such that the skin surface 26 is cooler than the region 32 and the temperature increases in a temperature gradient from the skin surface 26 to the region 32.

The handpiece 12 is equipped with a valve 35 used to deliver a metered amount of cryogen, as a spray, a stream, or another physical form, to the treatment electrode 20. In the representative embodiment, the metered amounts of cryogen are expelled or discharged from the nozzle 62 as cryogen pulses directed toward the backside 51 of the treatment electrode 20 and, in particular, toward the conductor region 24 of treatment electrode 20. Various duty cycles of cooling and heating that rely on cooling and high frequency energy transfer from the treatment electrode 20 are utilized contingent upon the type of treatment and the desired type of therapeutic effect. The cooling and heating duty cycles may be controlled and coordinated by operation of the system controller 18.

Typically, the patient's epidermis is held at a temperature that is below a therapeutic temperature in order to prevent harm to the epidermis. The cryogen spray is used to pre-cool the patient's epidermis, before powering the treatment electrode 20, by heat transfer between the treatment electrode 20 and the epidermis. The cooling creates a reverse thermal gradient in the tissue 30 such that the temperature of the tissue 30 at the skin surface 26 is cooler than the temperature of the tissue 30 within the epidermis or dermis. As a result, the high frequency energy delivered to the tissue 30 fails to heat all or a portion of the patient's epidermis to a temperature sufficient to cause significant epidermal thermal damage. The region 32 of tissue 30 that is not significantly cooled by pre-cooling will volumetrically warm up to therapeutic temperatures, which cause a desired therapeutic effect. The amount and/or duration of pre-cooling may be used to select the protected depth of untreated tissue 30 between the region 32 and the skin surface 26. The metered delivery of cryogen by the valve 35 to the treatment tip 14 may also be used to cool portions of the tissue 30 during and/or after heating by the high frequency energy transferred from the treatment electrode 20. Post-cooling may prevent or reduce heat delivered deeper into the region 32 of the tissue 30 from conducting upward and heating shallower tissue regions, such as the epidermis, to temperatures which could thermally damage the epidermis even though external energy delivery to the targeted tissue 30 has ceased.

The handpiece 12 includes a display 93, controls 95, 96 that scroll different functions on the display 93, controls 97, 98 used to respectively increase and reduce the setting for the function currently on the display 93, and a control to engage a changed setting. The display 93 may be used to display information including, but not limited to, energy delivered, tissue impedance, duration, and feedback on procedure technique. The availability of the information displayed on the display 93 may conveniently eliminate the need to display identical information on the interface devices 49, or may duplicate displayed information by the interface devices 49. By displaying information at the handpiece 12, the operator can focus on the procedure without diverting his attention to glance at information displayed by the display on the interface devices 49. In one embodiment, the display 93 may constitute a thin, flat liquid crystal display (LCD) comprised of a light source or reflector and an arbitrary number of color or monochrome pixels arrayed in front of the light source or reflector. A driver circuit (not shown) is provided to control the operation of the display 93.

Figure 4:
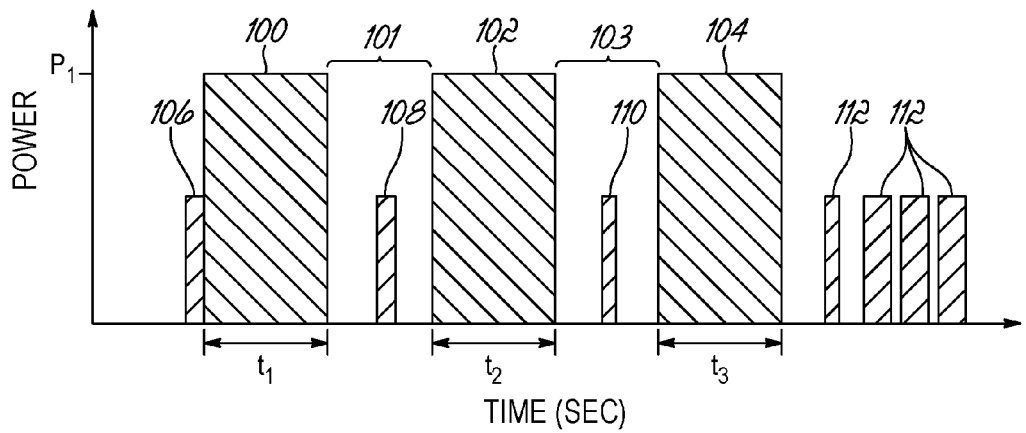
FIG. 4 is a graphical view that depicts the use of the treatment system of FIG. 1 to deliver coordinated pulses of applied high frequency energy and cryogen spray pulses in accordance with an embodiment of the invention.

With reference to FIG. 4, a protocol is shown in which the high frequency power delivered from the generator 16 to the treatment electrode 20 for each treatment location on the skin surface 26 (each repetition) is modulated into multiple discrete pulses 100, 102, 104 as opposed to being applied as a continuous pulse over a total treatment time, T. A treatment repetition is constituted by contacting the treatment electrode 20 with the skin surface 26, applying power to the treatment electrode 20 for the characteristic treatment time, T, that takes into account the protocol of FIG. 4, and lifting the treatment electrode 20 from the skin surface after the protocol concludes and after the treatment time, T, has concluded. In a preferred embodiment, the treatment electrode 20 is maintained stationary during over the entire duration of the repetition and any perceived movement is unintentional.

The pulses 100, 102, 104 have a maximum power, $P_1$, characterized by a constant current and a respective duration $t_1, t_2, t_3$ over which the maximum power, $P_1$, is applied. In the representative embodiment, the maximum pulse power, $P_1$, is constant, the pulse duration $t_1, t_2, t_3$ is uniform, and the power drops to zero in the time gaps between adjacent pairs of pulses 100, 102, 104. The pulses 100, 102, 104 are temporally separated such that the continuity is interrupted by time gaps 101, 103 between adjacent pairs of the pulses 100, 102, 104 and the pulses 100, 102, 104 are discontinuous. During the time gaps 101, 103, the system controller 18 interrupts the delivery of the electromagnetic energy so that electromagnetic energy is not delivered to the patient's tissue in the time gaps 101, 103. For example, the duration of each of the pulses 100, 102, 104 may nominally be 300 milliseconds and each of the intervening time gaps 101, 103 may be 50 milliseconds so that power delivery effectively occurs with periodic interruptions introduced by time gaps 101, 103 over a one (1) second time period. The processor 36 of the system controller 18 executes the generator control program 46 resident as an application in the memory 38 in order to issue commands that control the operation of the generator 20 to provide the power pulses 100, 102, 104.

A cryogen pulse 106 is delivered before the initial power pulse 100 and operates to pre-cool the tissue 30 at the treatment site. Cryogen pulses 108, 110 are respectively synchronously delivered in the time gap 101 between power pulses 100, 102 and in the time gap 103 between power pulses 102, 104. After power delivery from all power pulses 100, 102, 104, a train of additional cryogen pulses 112 is delivered to post-cool the tissue 30 at the treatment site. The processor 36 of the system controller 18 executes the cryogen control program 46 resident as an application in the memory 38 in order to issue commands that control the operation of the cryogen supply 15 and the valve 35 to provide the cryogen pulses 106, 108, 110, 112. The cryogen pulses 106, 108, 110, 112 operate to cool the tissue 30 between region 32 and the skin surface 26 to a non-therapeutic temperature during the course of the procedure. The cryogen pulses 106, 108, 110 are depicted in the representative embodiment as initiating and concluding before the initiation of the respective one of the power pulses 100, 102, 104. However, in alternative embodiments, the timing may be altered such that the cryogen pulses 106, 108, 110 at least partially overlap temporally with the power pulses 100, 102, 104. For example, the onset of each pulse 106, 108, 110 in the coolant delivery may coincides with the onset of the respective one of the power pulses 100, 102, 104.

Various duty cycles of cooling and heating by cryogen delivery in cryogen pulses 106, 108, 110, 112 and high frequency energy transfer in power pulses 100, 102, 104 are utilized depending on the type of treatment and the desired type of therapeutic effect. The cooling and heating duty cycles may be controlled and coordinated by operation of the system controller 18 and in conjunction with user input via user interface devices 49 at the system controller 18, controls 96-99 at the handpiece 12, and software settings in the generator and cryogen control programs 44, 46.

Various parameters may be adjusted in the generator control program 44 and cryogen control program 46 to implement an interleaved pattern of power and cryogen pulses for each treatment repetition as shown in FIG. 4. The current limit for the high frequency power in pulses 100, 102, 104 may be set to a value in the range of about 0.3 amperes to about 1.6 amperes with 0.01 ampere adjustment increment, which varies according to the treatment and is specific to the type of treatment tip 14. The maximum energy permitted to be delivered by a set of power pulses 100, 102, 104 during a repetition may range from 10 Joules to 300 Joules with a precision of 1 Joule using electrodes having a size ranging from 1 $cm^2$ to 20 $cm^2$.

The duration of each of the high frequency power pulses 100, 102, 104 may be set within a range of 200 milliseconds to 300 milliseconds with an adjustment increment of 10 milliseconds, and the time gaps 101, 103 between consecutive pulses 100, 102, 104 in each repetition may be set to a value in the range of 10 milliseconds to 50 milliseconds with an adjustment increment of 10 milliseconds. With the recognition that the number of pulses and pulse and gap lengths may vary, the frequency for the pulsing of pulses 100, 102, 104 may range from 1 Hz to 10 Hz, which is more than four orders of magnitude less than the 200 kHz to 20 MHz RF operating frequency for generator 16.

The delivery of the high frequency energy may be constrained by the current limit selection and the maximum power selection. The selected maximum power is usually reached within a fraction of the pulse duration and is stabilized by a Proportional-Integral-Derivative (PID) feedback loop. In addition, the current-limiting mode based upon the selected current limit may begin to function only after the target power has been reached, and takes an additional fraction of the pulse duration to stabilize the current delivery. Hence, the square pulse shape for pulses 100, 102, 104 is diagrammatically ideal and ignores transient effects in delivery.

The duration of each of the cryogen pulses 106, 108, 110 before and between each set of high frequency energy pulses may be set within a range of 2 milliseconds to 49 milliseconds with an adjustment increment of 1 millisecond and the train of cryogen pulses 112 after the delivery of the high frequency pulses of energy may range from 2 milliseconds to 200 milliseconds with an adjustment increment of 1 millisecond. The maximum temperature measured by the sensors 52 and allowed to persist while delivering the power pulses 100, 102, 104 may range from 0° C. to 50° C. with an adjustment increment of 1° C. In response to this maximum temperature selection and during energy delivery, the system controller 18 may compare the selected maximum temperature with a median temperature determined from the readings supplied by the sensors 52. The sensors 52 may supply these readings at regular time intervals to the system controller 18. If the selected maximum temperature is exceeded and sustained over a given time period, corrective measures may be taken. For example, power delivery may be discontinued, the pulses 112 may be triggered for delivery, and an audible warning tone may be sounded.

Figure 5:
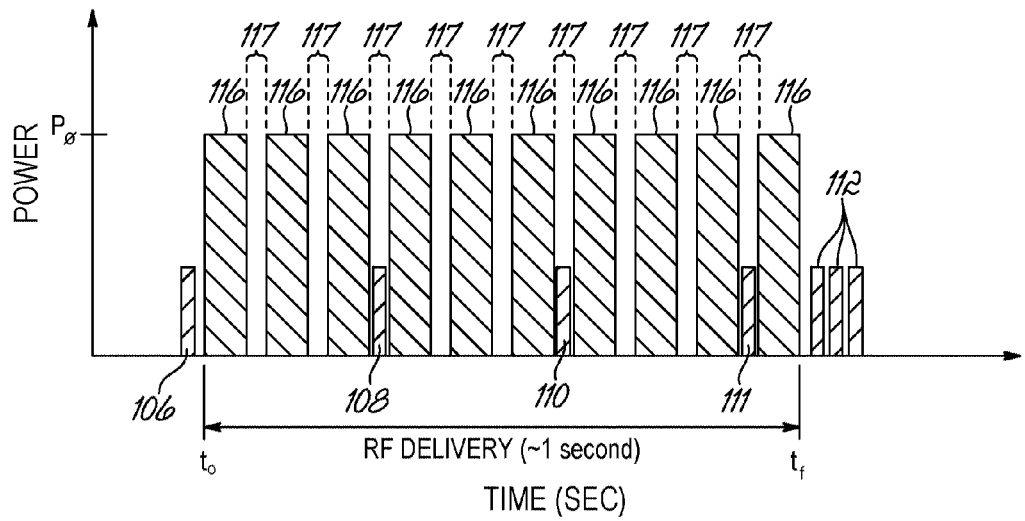
FIG. 5 is a graphical view similar to FIG. 4 that depicts the use of the treatment system of FIG. 1 to deliver coordinated pulses of applied high frequency energy and cryogen spray pulses in accordance with an alternative embodiment of the invention

As mentioned above, the number of power pulses may differ from that shown in FIG. 4. For example and with reference to FIG. 5, the number of power pulses 116 has been increased to ten (10) and an additional cryogen pulse 111 is provided between the final two power pulses 116. The cryogen pulses 108, 110 occur after every three of the power pulses 116, which have a maximum power, $P_0$. As a numerical example, the pulse duration for each pulse 116 may be 100 milliseconds and the time gaps 117 may be about 11 milliseconds for a power delivery time of one (1) second. Additional embodiments of the invention may vary the number of power pulses, the power and duration of each individual power pulse, the number of cryogen pulses, and the duration of each cryogen pulse.

Figure 6:
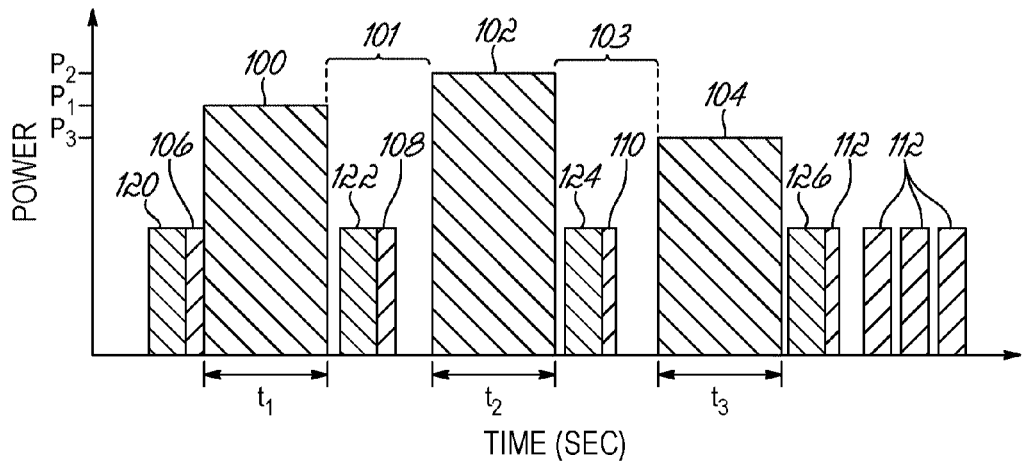
FIG. 6 is a graphical view similar to FIG. 4 that depicts the use of the treatment system of FIG. 1 to deliver coordinated pulses of applied high frequency energy and cryogen spray pulses in accordance with an alternative embodiment of the invention in which the power in each pulse is adjusted before application in conjunction with a measurement of an attribute such as temperature, impedance, etc.

With reference to FIG. 6, the procedure protocol of FIG. 4 has been modified to introduce sensor readings 120, 122, 124, 126 from, for example, one or more of the sensors 52. The output of the sensors 52, such as a property or attribute like skin temperature or impedance, at each of the sensor readings 120, 122, 124 is used by the system controller 18 to determine the high frequency power to be applied in each of the power pulses 100, 102, 104. The power level, $P_1$, $P_2$, $P_3$, for each of the respective pulses 100, 102, 104 may be specified by adjusting a duty cycle for the delivered power based upon the output from the sensors 52. In one embodiment in which the sensors 52 measure temperature, the system controller 18 may average the temperature readings from the sensors 52 and rely on the average in adjusting the power level for the different pulses. The system controller 18 implements the power modulation control program 44 as a software routine to provide the power impulses characteristic of the power chopping illustrated in FIG. 6. Specifically, the system controller 18 may include a pulse-width modulation (PWM) module that is capable of causing the generator 16 to deliver the output high frequency power in pulses of predetermined duration and predetermined amplitude at a desired frequency. The PWM of the high frequency signal from generator 16 involves the modulation of the duty cycle to control the amount of power sent to the treatment electrode 20.

In use to perform a treatment procedure, the physician selects a type of treatment tip 14 based on the procedure to be performed and the size of the surface area on the patient to be treated, as well as the depth of cooling and heating desired for the treatment procedure. After choosing the treatment tip 14 and attaching it to the handpiece 12, the physician marks the intended treatment area on the patient with a grid of removable markings that are easily wiped away post-procedure. Each discrete square in the grid corresponds approximately to the size of the portion 60 of the treatment electrode 20 that is placed in direct contact with the skin surface 26. The markings operate as a placement guide on the patient's skin surface 26 for the treatment procedure. The return electrode 56 is attached to the patient to supply the current path for the high frequency current back to the generator 16.

After the optional application of a conductive fluid, each square within the grid is sequentially treated with high frequency energy delivered from the treatment electrode 20. Specifically, at each grid square, the physician lands the treatment electrode 20 directly against the patient's skin and actuates the activation button 54 on the handpiece 12. The treatment electrode 20 transmits high frequency energy to the tissue 30 beneath the skin surface 26 while serving as a contact cooling membrane for the cryogen. Information about skin temperature and contact, treatment force or pressure against the skin, cooling system function, and other types of relevant data, such as impedance may be supplied from the treatment tip 14 to the system controller 18 to precisely and safely control the high frequency energy and coolant delivery to each treatment site in the grid. Cooling the epidermis limits the temperature to lessen the likelihood of thermal damage to the epidermis. While maintaining contact with the skin surface 26 during each repetition, power and cryogen are delivered according to the one of the protocols shown in FIGS. 4-6, or a different protocol consistent with the principles of the invention.

After energy delivery is completed during each repetition, the handpiece 12 is maneuvered to lift the portion 60 of the treatment electrode 20 from the skin surface 26. The handpiece 12 and treatment tip 14 are moved among subsequent treatment locations in the grid and energy is delivered in a similar manner for treating large regions on the patient, such as the patient's face. Multiple passes over the entire grid of the treatment zone, separated in time by a quiescent period of a few minutes, may be used to enhance the treatment, as is understood by persons skilled in the art. Multiple treatments, which are separated temporally by a lengthier healing period, may be needed for a successful treatment that supplies the desired cosmetic effect.

Dividing the treatment at each treatment zone and for each repetition into a plurality of pulses is effective to decrease the sensation of pain experienced by the patient from the delivery of electromagnetic energy during a treatment procedure. The human nervous system is believed to be confused by the periodic interruption of the applied power which results in a lower level of perceived pain, which allows for the delivery of higher amounts of high frequency energy while minimizing the associated pain perceived by the patient. Effectively, the acute pain during each repetition is converted into a form of tolerable, chronic, heat-related discomfort after the repetition.

References herein to terms such as "vertical", "horizontal", etc. are made by way of example, and not by way of limitation, to establish a frame of reference. It is understood that various other frames of reference may be employed for describing the invention without departing from the spirit and scope of the invention. It is also understood that features of the invention are not necessarily shown to scale in the drawings. Furthermore, to the extent that the terms "composed of", "includes", "having", "has", "with", or variants thereof are used in either the detailed description or the claims, such terms are intended to be inclusive and open-ended in a manner similar to the term "comprising."

It will be understood that when an element is described as being "attached", "connected", or "coupled" to another element, it can be directly connected or coupled to the other element or intervening elements may be present. In contrast, when an element is described as being "directly attached", "directly connected", or "directly coupled" to another element, there are no intervening elements present.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of applicants' general inventive concept.

What is claimed is:

1. A method of operating a tissue treatment apparatus to transcutaneously treat tissue located beneath a skin surface of a patient with electromagnetic energy delivered from a treatment electrode, the method comprising:

contacting a portion of the treatment electrode with the skin surface in a stationary relationship;

while maintaining the stationary contact between the portion of the treatment electrode and a treatment zone on the skin surface, delivering the electromagnetic energy from the treatment electrode through the skin surface to the tissue over a treatment time in a plurality of power pulses having a first duration and a time gap between consecutive power pulses effective to decrease a sensation of pain experienced by the patient; and during the treatment time, delivering a plurality of cryogen pulses to the portion of the treatment electrode that have a second duration that is less than the first duration of the power pulses.

2. The method of claim 1 wherein a power of the electromagnetic energy delivered in each of the power pulses has a constant magnitude.

3. The method of claim 1 further comprising:
measuring an attribute of the tissue; and
adjusting a power of the electromagnetic energy delivered in each of the power pulses based upon the measured attribute.

4. The method of claim 3 wherein the measured attribute is tissue temperature or tissue impedance.

5. The method of claim 1 wherein the cryogen pulses cool the portion of the treatment electrode, and further comprising:
communicating the cooling of the portion of the treatment electrode to the skin surface contacted by the portion of the treatment electrode so that a portion of the tissue underlying the skin surface is cooled.

6. The method of claim 1 further comprising:
cooling the tissue using each cryogen pulse.

7. The method of claim 1 wherein the electromagnetic energy has an operating frequency ranging from 200 kHz to 20 MHz, and the power pulses occur with a frequency in a range of 1 Hz to 10 Hz.

8. The method of claim 1 wherein the power pulses occur at a frequency that is more than four orders of magnitude less than an operating frequency for the electromagnetic energy.

9. The method of claim 1 wherein delivering the plurality of cryogen pulses to the portion of the treatment electrode comprises:
delivering the cryogen pulses to the portion of the treatment electrode during the time gaps between consecutive pairs of the power pulses.

10. The method of claim 9 wherein delivering the cryogen pulses to the portion of the treatment electrode during the time gaps between the consecutive pairs of power pulses further comprises:
delivering the cryogen pulses to the portion of the treatment electrode in the time gap between each of the consecutive pairs of the power pulses.

11. The method of claim 10 wherein the cryogen pulses cool the portion of the treatment electrode, and further comprising:
communicating the cooling of the portion of the treatment electrode to the skin surface contacted by the portion of the treatment electrode so that a portion of the tissue underlying the skin surface is cooled.

* * * * *